United States Patent
Xie et al.

(10) Patent No.: US 11,147,773 B2
(45) Date of Patent: Oct. 19, 2021

(54) CHLOROQUINE GEL AND PREPARATION METHOD AND APPLICATION THEREOF

(71) Applicants: GUANGZHOU HYBRIBIO MEDICINE TECHNOLOGY LTD., Guangdong (CN); GUANGZHOU HYBRIBIO BIOTECH LTD., Guangdong (CN)

(72) Inventors: Longxu Xie, Guangdong (CN); Xiangling Li, Guangdong (CN); Manli Yuan, Guangdong (CN); Ting Wang, Guangdong (CN); Jianyu Wang, Guangdong (CN)

(73) Assignees: GUANGZHOU HYBRIBIO MEDICINE TECHNOLOGY LTD., Guangdong (CN); GUANGZHOU HYBRIBIO BIOTECH LTD., Guangdong (CN)

( * ) Notice: Subject to any disclaimer, the term of this patent is extended or adjusted under 35 U.S.C. 154(b) by 0 days.

(21) Appl. No.: 16/978,713

(22) PCT Filed: Nov. 4, 2019

(86) PCT No.: PCT/CN2019/115216
§ 371 (c)(1),
(2) Date: Sep. 7, 2020

(87) PCT Pub. No.: WO2020/114166
PCT Pub. Date: Jun. 11, 2020

(65) Prior Publication Data
US 2020/0397713 A1  Dec. 24, 2020

(30) Foreign Application Priority Data
Dec. 4, 2018 (CN) .......................... 201811474701.3

(51) Int. Cl.
| A61K 9/51 | (2006.01) |
| A61P 31/10 | (2006.01) |
| A61K 9/00 | (2006.01) |
| A61K 9/06 | (2006.01) |
| A61K 31/4706 | (2006.01) |

(52) U.S. Cl.
CPC .......... *A61K 9/5161* (2013.01); *A61K 9/0034* (2013.01); *A61K 9/06* (2013.01); *A61K 31/4706* (2013.01); *A61P 31/10* (2018.01)

(58) Field of Classification Search
None
See application file for complete search history.

(56) References Cited

U.S. PATENT DOCUMENTS

| 7,309,500 B2 * | 12/2007 | Kim ...................... A61K 9/146 424/489 |
| 2015/0303461 A1 * | 10/2015 | Li ........................... H01M 4/48 429/231 |

FOREIGN PATENT DOCUMENTS

| CN | 102488659 | 6/2012 |
| CN | 104703601 | 6/2015 |
| CN | 109288816 | 2/2019 |
| WO | 2007025767 | 3/2007 |

OTHER PUBLICATIONS

CN 102488659; wherein a machine translation is provided (Year: 2012).*
CN 104703601; wherein a machine translation is provided (Year: 2015).*
Ko et al (Preparation and characterization of chitosan microparticles intended for controlled drug delivery. International Journal of Pharmaceutics. 249 (2002) 165-174 (Year: 2002).*
Wu et al (In situ preparation of magnetic Fe3O4-chitosan nanoparticles for lipase immobilization by cross-linking and oxidation in aqueous solution. Bioresource Technology. 100 (2009) 3459-3464) (Year: 2009).*
"International Search Report (Form PCT/ISA/210) of PCT/CN2019/115216," dated Feb. 7, 2020, pp. 1-4.

* cited by examiner

*Primary Examiner* — Jake M Vu
(74) *Attorney, Agent, or Firm* — JCIPRNET

(57) ABSTRACT

A chloroquine gel and a preparation method and application thereof. A chloroquine nanosphere includes a water-soluble nanosphere carrier, and chloroquine or a chloroquine derivative, wherein a mass ratio of the chloroquine or the chloroquine derivative to the water-soluble nanosphere carrier is no more than 1:3.

4 Claims, 8 Drawing Sheets

CHLOROQUINE GEL AND PREPARATION METHOD AND APPLICATION THEREOF

CROSS-REFERENCE TO RELATED APPLICATION

This application is a continuation of international PCT application serial no. PCT/CN2019/115216, filed on Nov. 4, 2019, which claims the priority benefit of Chinese application no. 201811474701.3, filed on Dec. 4, 2018. The entirety of each of the above-mentioned patent applications is hereby incorporated by reference herein and made a part of this specification.

BACKGROUND

Technical Field

The present invention belongs to the field of biological medicine technologies, and more particularly, relates to a chloroquine gel for treating external genitalia infection and other cutaneous warts and a preparation method and application thereof.

Description of Related Art

Genital infections, also called sexually transmitted diseases, refer to a group of diseases mainly transmitted by sexual contact. More than 20 infectious diseases caused by sex behaviors or similar sex behaviors are included in the category of genital infections internationally. Since the 1980s, floating population has been increasing day by day. With the change of sexual concept, unsafe sex behaviors have increased. Reproductive tract infection and sexually transmitted infection are increasing in China, and have spread from the coast to the inland and developed from the city to the countryside, so that the situation is quite severe. According to statistics, there are about 400,000 AIDS patients in China today, HIV infection is about 1 in 1,000, and about hundreds of people are infected every day, with characteristics of a large sexual transmission ratio and the transmission from a high-risk group to a general group. According to statistics, the number of patients suffering from external genitalia infection of both sexes in China is still increasing year by year in recent years, an incidence rate in many areas ranks second and third in an order of infectious diseases, an incidence rate of lower genital tract infection among married women is as high as 50%, and 70% of women at least suffered from vulvovaginal candidiasis once in their lifetime, 5% to 10% of which suffered from recurrent vaginal candidiasis and 90% of which were infected with human papillomavirus. An incidence rate of the external genitalia infection of both sexes is increasing so rapidly that a difficulty in control has become a serious social and public health problem to the world. Therefore, effective prevention and treatment of the external genitalia infection of both sexes have become very serious and urgent tasks at present.

The external genitalia infection is mainly treated by aiming at a pathogen in modern medicine. In terms of prevention and treatment, there are many kinds of pathogenic microorganisms causing the reproductive tract infection, and the variation and drug resistance of the pathogen make it extremely difficult to select an antibiotic medicine to prevent the reproductive tract infection. At present, in clinical practice, the treatment of the external genitalia infection is mostly based on antibiotic or disinfectant administration. However, since irritation of a disinfectant to a local mucosa destroys an environment in a vagina, the use of the disinfectant is limited, and the disinfectant is usually only suitable for local treatment. For bacterial genital infection, an antibiotic therapy often brings drug resistance and side effects. Therefore, it is of great significance to develop a new and highly effective medicine for external use with antibacterial and antiviral effects for the effective prevention and treatment of the external genitalia infection.

Chloroquine has always been used as a medicine to prevent and treat plasmodium infection, and is often used in gene transfection experiments to improve a transfection efficiency. The high-concentration chloroquine is found to have an effect of inhibiting and killing cryptococcus in vitro through in-vitro studies, and effects of the chloroquine on two varieties of the cryptococcus are not different; and meanwhile, the chloroquine can enhance an anti-cryptococcal ability of amphotericin B and has a synergistic antibacterial effect with the amphotericin B. At present, many studies focus on an anti-HIV activity of the chloroquine. Studies have shown that the chloroquine has a broad-spectrum anti-HIV activity, and the chloroquine not only is aimed at a laboratory strain B evolved by HIV-1, but also has a great effect on primary isolates A, B, C, D and E evolved by HIV-1. It seems that a main mechanism of an anti-HIV effect of the chloroquine is to inhibit glycosylation of a gp120 virus envelope protein, resulting in that a newly generated virus particle has a severely reduced infectivity. Meanwhile, it is believed in studies that the chloroquine is an aminoquinine membrane-penetrating agent, which can be embedded into a double-stranded DNA and change a double helix form of a DNA by unwinding. It is believed in bacteriological studies that the chloroquine can be used as a kind of intercalators such as acridine orange and ethidium bromide, which can selectively inhibit a covalent bond of a small plasmid DNA, and by changing a density of DNA supercoils, the closure of the supercoil can be changed, thus inhibiting the proliferation of bacteria and virus-infected cells. A DNA of a human papillomavirus (HPV) causing a cervical cancer is such a plasmid, which is a supercoiled complex DNA, and performs DNA replication and RNA transcription. In turn, the chloroquine has been proved to be able to inhibit the plasmid DNA and interfere with an activity of DNA polymerase by changing a superhelix density of the plasmid DNA. Due to the alkalescence, the chloroquine has been proved to cause mitochondrial dysfunction, such as accumulation of endosomes/lysosomes, change of a pH value and possible apoptosis. In addition, the chloroquine has been proved to reactivate inactivated P53 (HPV degradation/P53 inactivation), be connected to melanin (production of melanin occurs on the same layer of skin as HPV replication: a basal layer of epidermis), and prevent release of iron ions (iron catalyst/energy dependence of HPV during replication). Iron is necessary for DNA replication, and the iron also acts as an electronic catalyst in transportation and storage of oxygen. However, the iron is also a vital substance for pathogen survival and virus replication. Inhibition of iron particles is also an important mechanism for the chloroquine to kill viruses and virus-infected cells.

At present, there's no medicine of chloroquine for external use, especially the medicine that has no external preparation with less irritation and wider curative effect. In clinical application, the chloroquine is mainly used to treat an acute malaria attack and control a malaria symptom. The chloroquine can also be used for treating hepatic amebiasis, clonorchiasis, paragonimiasis, connective tissue disease, etc. The chloroquine can also be used for treating photosensitive diseases such as erythema solare disease. A tablet and an injection are used for treating malaria with large dosage and long course of treatment, which may have serious side effects on gastrointestinal tract and skin. In addition, the chloroquine has certain irritation on skin, causing skin damage and various types of rashes. Therefore, how to reduce the irritation of the chloroquine and the side effects, and improve an application value of the chloroquine by changing a dosage form has become the main problem at present.

A medicine microsphere refers to a tiny spherical entity formed by medicine dispersion or adsorption in a high-molecular polymer matrix. A microsphere preparation has a long-acting, sustained-release or targeted effect, which can greatly improve convenience and compliance of patients in medication, with outstanding advantages in clinic, so that the preparation is a potential dosage form. In addition, a microsphere preparation product has a great added value and a broad market prospect, and has become a hot spot in medicine research and development in recent years.

SUMMARY

An objective of the present invention is to overcome the defects in the prior art above, and provide a chloroquine nanosphere, which selects a natural polymer compound as a nanosphere carrier, has a simple preparation process and a small side effect of a product, gives full play to a synergistic effect of chloroquine and the nanosphere carrier, has obvious anti-inflammatory, antibacterial and antiviral effects, reduces irritation of the chloroquine to skin, promotes wound healing, can control a release speed of a medicine, and overcomes defects of a weak antibacterial effect of the existing microsphere carrier and large irritation of the chloroquine.

Another objective of the present invention is to provide a preparation method for the chloroquine nanosphere applied to external genitalia and other cutaneous warts.

One another objective of the present invention is to provide a new application for the chloroquine nanosphere above.

Still another objective of the present invention is to provide a product for preventing and treating external genitalia infection and/or other cutaneous warts.

The objectives of the present invention above are achieved through the following technical solutions.

A chloroquine nanosphere includes a water-soluble nanosphere carrier, and chloroquine or a chloroquine derivative.

The inventor unexpectedly discovers that the nanosphere which is prepared by combining the water-soluble nanosphere carrier with the chloroquine or the chloroquine derivative, has a long action time, a mucosal adhesiveness, a local retention and a self-degradability, reduces irritation of the chloroquine, has no irritation on the external genitalia, overcomes defects of a large side effect and inconvenient use in an existing external genitalia infection treatment method at the same time, and can effectively solve a side effect and a medicine resistance of the chloroquine; the nanosphere of the present invention can effectively prevent or treat external genitalia infection and other cutaneous wart diseases, such as vaginitis, flat warts and the like, and even has a remarkable synergistic effect; and not only an application range of the chloroquine is expanded, but also a phenomenon of medicine resistance caused by abuse of existing antibacterial medicines is reduced.

The present invention further relates to a preparation method for the chloroquine nanosphere above, which includes the following steps:

S1: after dissolving the water-soluble nanosphere carrier, adding the chloroquine or the chloroquine derivative, and evenly mixing and stirring to form an aqueous phase, wherein a mass ratio of the chloroquine or the chloroquine derivative to the water-soluble nanosphere carrier is no more than 1/3;

S2: adding an emulsifier into an oil phase matrix to form an oil phase; adding the aqueous phase into the oil phase, wherein a volume ratio of the aqueous phase to the oil phase is 1:1 to 1:6; and emulsifying at 10000-20000 r/min for 10-30 minutes to obtain a nanosphere emulsion; and S3: adding a precipitant into the nanosphere emulsion, after evenly mixing, standing for 2-8 minutes, then dehydrating, performing high-speed centrifugation and cleaning, and drying to obtain the chloroquine nanosphere.

Preferably, a mass ratio of the chloroquine or the chloroquine derivative to the water-soluble nanosphere carrier ranges from 1:3 to 1:5.

More preferably, the mass ratio of the chloroquine or the chloroquine derivative to the water-soluble nanosphere carrier is 1:3.

Preferably, the chloroquine derivative is selected from one or more of hydroxychloroquine, chloroquine phosphate and chloroquine sulfate.

Preferably, a loading rate of the chloroquine or the chloroquine derivative ranges from 3.0% to 21.6%.

More preferably, the loading rate of the chloroquine or the chloroquine derivative is 12.5%.

Preferably, the water-soluble nanosphere carrier is selected from one or more of water-soluble chitosan, water-soluble carrageenan and water-soluble starch.

Preferably, the water-soluble nanosphere carrier is the water-soluble chitosan.

More preferably, a deacetylation degree of the water-soluble chitosan ranges from 80% to 95%, and a viscosity-average molecular weight thereof ranges from 3000 to 5000.

Preferably, the volume ratio of the aqueous phase to the oil phase in the step S2 is 1:3.

Preferably, the high-speed centrifugation in the step S3 is performed at 1500-2000 r/min for 5-10 minutes.

More preferably, the high-speed centrifugation in the step S3 is performed at 1500 r/min for 10 minutes.

Preferably, in the step S3, the precipitant is added into the nanosphere emulsion at a speed of 1 to 5 drops per second.

Preferably, a volume ratio of the emulsifier to the precipitant is (1-1.5):(30-50).

More preferably, the volume ratio of the emulsifier to the precipitant is 1:50.

Preferably, the oil phase matrix is vegetable oil; and the precipitant is an alkaline organic phase.

More preferably, the alkaline organic phase is a sodium hydroxide-n-propanol mixed solution.

More preferably, a pH value of the alkaline organic phase ranges from 8.5 to 10.0.

More preferably, the pH value of the alkaline organic phase is 9.0.

Preferably, the vegetable oil is selected from one or more of corn oil, olive oil, peanut oil, soybean oil, rapeseed oil and other vegetable oils.

Preferably, the emulsifier is selected from one or more of Tween-20, Tween-80 and Span 80.

Application of the chloroquine nanosphere above in preparing an antibacterial and/or antiviral product, and application of the chloroquine nanosphere above in preparing a product for preventing and treating external genitalia infection and/or other cutaneous warts are also included in the scope of protection of the present invention.

The product including the chloroquine nanosphere above can obviously reduce skin irritation of the chloroquine, promote wound healing, play a slow release effect, and improve a biological activity at the same time, and is applied to treat external genitalia infection and/or other cutaneous warts.

Preferably, the external genitalia infection includes viral vaginitis, condyloma acuminatum, bacterial vaginosis, fungal-infectious vaginitis or trichomonal vaginitis.

Preferably, the other cutaneous warts include flat warts and warts at non-genital parts caused by HPV infection.

The chloroquine nanosphere has good therapeutic effects on the external genitalia infection including viral vaginitis, condyloma acuminatum, bacterial vaginosis, fungal-infectious vaginitis or trichomonal vaginitis, and the other cutaneous warts including flat warts and warts at non-genital parts caused by HPV infection.

The present invention further provides a product for preventing and treating external genitalia infection and/or other cutaneous warts, which includes chloroquine or a chloroquine derivative, and further includes one or more of water-soluble chitosan, water-soluble carrageenan and water-soluble starch.

Preferably, a mass ratio of the chloroquine or the chloroquine derivative to the water-soluble chitosan, the water-soluble carrageenan or the water-soluble starch is not more than 1/3.

More preferably, the mass ratio of the chloroquine or the chloroquine derivative to the water-soluble chitosan, the water-soluble carrageenan or the water-soluble starch ranges from 1:3 to 1:5.

More preferably, the mass ratio of the chloroquine or the chloroquine derivative to the water-soluble chitosan, the water-soluble carrageenan or the water-soluble starch is 1:3.

Further, in a preferred embodiment of the present invention, the product for preventing and treating external genitalia infection and/or other cutaneous warts includes the chloroquine nanosphere above.

More preferably, the chloroquine nanosphere accounts for 1% to 6% of a total weight of the product.

Further, in a preferred embodiment of the present invention, the product is gel, ointment, cream, effervescent tablet, vaginal tablet, capsule, film agent or suppository.

The product of the present invention can be processed into a semi-solid preparation such as gel, cream and the like, or a solid preparation such as tablet, effervescent tablet and the like; and the product of the present invention can obviously improve bitter taste and skin irritation of the chloroquine, promote wound healing, play a slow release effect and improve a biological activity at the same time.

Further, in a preferred embodiment of the present invention, the product is gel.

Compared with the prior art, the present invention has the following beneficial effects.

(1) According to the present invention, the water-soluble nanosphere carrier is combined with the chloroquine to prepare an external preparation with sterilization and anti-virus functions at the same time, which plays an obvious synergistic effect, has certain cleaning and killing effects on various bacteria and viruses, and cleaning and nursing effects on external genital organs for male and female, reduces inflammatory reactions of the external genitalia, can well improve skin irritation caused by the chloroquine, has no irritation on vaginal mucosa and penis, and has mucosal adhesiveness, local retention and self-degradability, and the preparation not only can prevent bacterial and viral infection, but also can promote micro wound healing, and can be used for effective treatment of external genitalia infection and warts, especially health care of external genitalia before and after sexual life, with an obvious effect, and a cool and comfortable effect.

(2) The present invention mainly uses the water-soluble nanosphere carrier combined with the synergist chloroquine as a main component. The prescription is stable, and a medicine exists in a form of nanosphere so that a detention time of the medicine at a treated part can be prolonged, enabling an action time to be longer, and improving a bioavailability and a therapeutic effect of the medicine. The medicine is simple and convenient in preparation method, easy in synthesis without toxic and side effects, and has high safety; moreover, industrial application of a new medicine can be performed, thus providing a new direction for development and application of an antibacterial-active and anti-viral-active medicine.

DESCRIPTION OF THE EMBODIMENTS

The invention is further described hereinafter with reference to the specific embodiments, but the embodiments are not intended to limit the invention in any form. Any simple modifications or substitutions made to the methods, steps or conditions of the invention without departing from the spirit and essence of the invention shall all fall within the scope of the present invention. Unless otherwise specified, the technical means used in the embodiments are conventional means well known to those skilled in the art.

The reagents and materials used in the following embodiments are commercially available unless otherwise stated.

Embodiment 1 Preparation of Chloroquine-Chitosan Nanosphere

1. Preparation Method

In S1, 3 g of water-soluble chitosan was dissolved into 100 mL of water, added with 1.0 g of chloroquine phosphate, and evenly mixed and stirred to form an aqueous phase, wherein a degree of deacetylation of the water-soluble chitosan was 80%, and a viscosity-average molecular weight thereof was 5000.

In S2, 300 mL of corn oil was used as an oil phase matrix, and 1 mL of an emulsifier Tween-20 was added into the oil phase matrix to form an oil phase; and the aqueous phase was added into the oil phase, wherein a volume ratio of the aqueous phase to the oil phase was 1:3, and then emulsification was performed at 15000 r/min for 30 minutes to obtain a nanosphere emulsion.

In S3, a sodium hydroxide-n-propanol mixed solution was used as a precipitant, 10 mL of n-propanol was firstly added with several drops of saturated sodium hydroxide solution to adjust a pH value to 9, then the mixed solution was evenly mixed and added into the nanosphere emulsion at a speed of 1 to 5 drops per second, a volume ratio of the emulsifier to the precipitant was controlled to be 1:50, then a mixture obtained was stood for 5 minutes, and added with a proper amount of n-propanol for dehydration; and then the mixture was centrifuged at 1500 r/min for 10 minutes, cleaned, and dried, thus obtaining the chloroquine-chitosan nanosphere.

Figure 1:
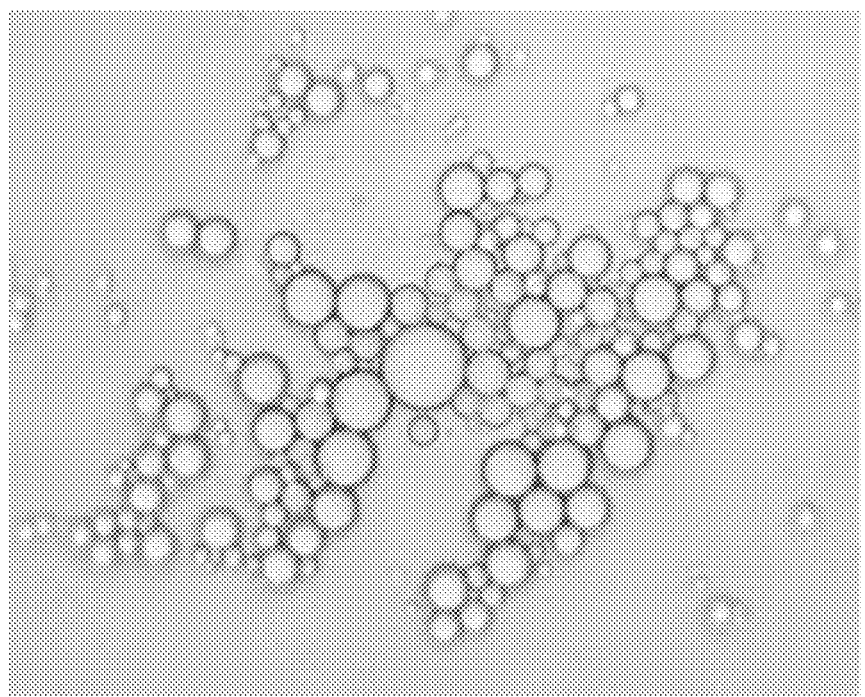
FIG. 1 shows a chloroquine-chitosan nanosphere.

2. Product Characterization (1) The prepared chloroquine-chitosan nanosphere is shown in FIG. 1, wherein a particle diameter of the prepared chloroquine-chitosan nanosphere ranges from 100 nm to 800 nm.

Figure 2:
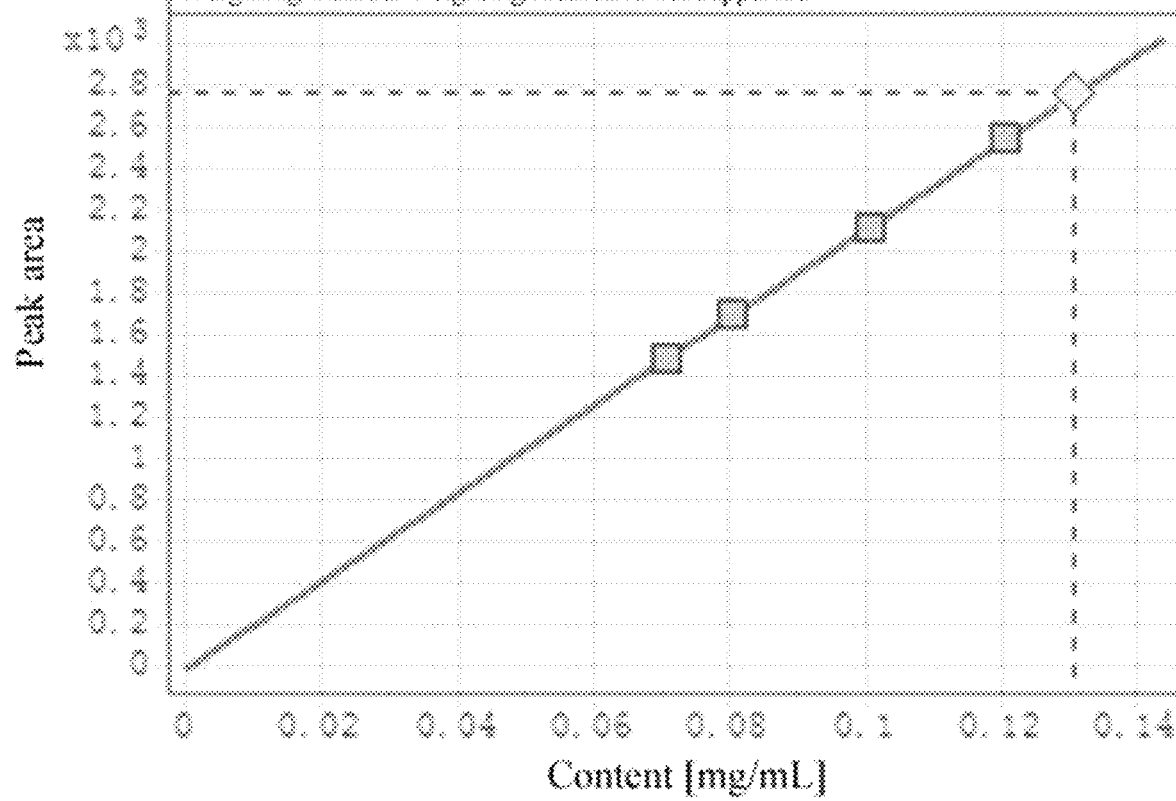
FIG. 2 is a standard curve for high-performance liquid-phase detection of chloroquine.
Figure 3:
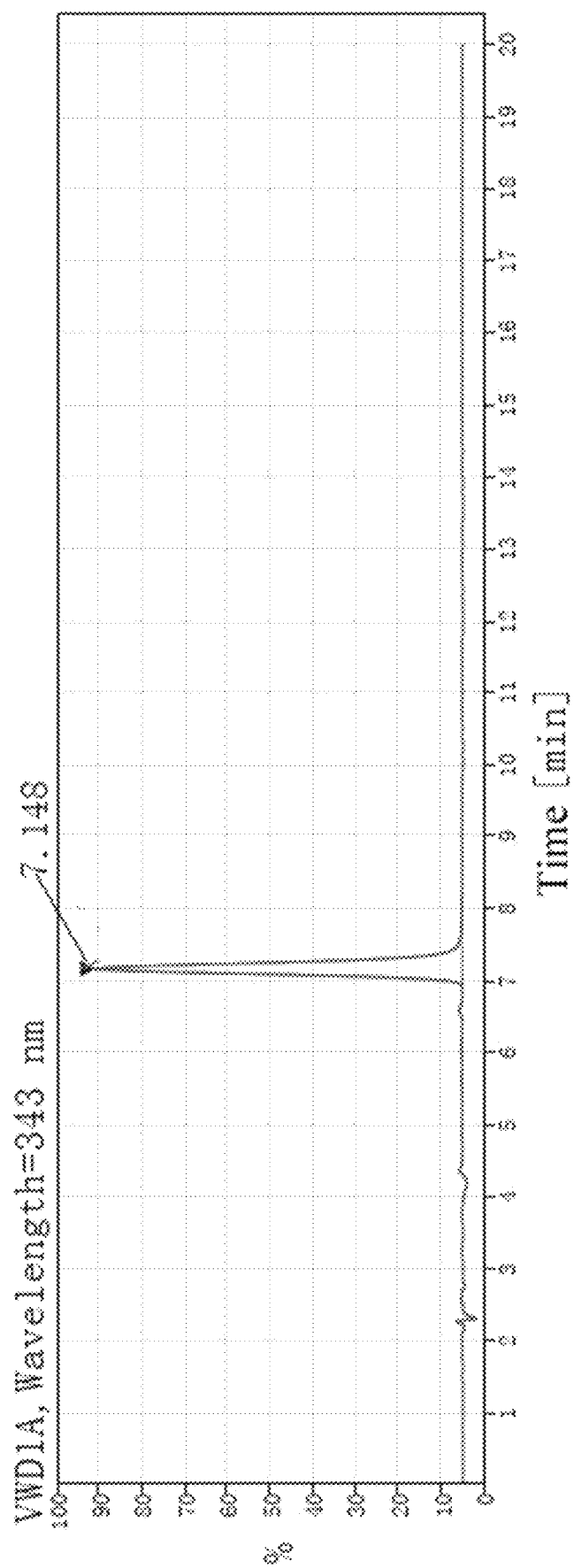
FIG. 3 shows a content of chloroquine in the chloroquine-chitosan nanosphere in high-performance liquid-phase detection.

(2) As shown in FIGS. 2 and 3, a loading rate of the chloroquine in the chloroquine-chitosan nanosphere is 12.5% via determination by high performance liquid chromatography.

Embodiment 2 Preparation of Chloroquine-Chitosan Nanosphere

1. Preparation Method

In S1, water-soluble chitosan was dissolved in water, then added with hydroxychloroquine, and evenly mixed and stirred to form an aqueous phase, and a mass ratio of the hydroxychloroquine to the water-soluble chitosan was controlled to be 1:5, wherein a degree of deacetylation of the water-soluble chitosan was 90%, and a viscosity-average molecular weight thereof was 3000.

In S2, 300 mL of corn oil was used as an oil phase matrix, and 1 mL of an emulsifier Tween-20 was added into the oil phase matrix to form an oil phase; and the aqueous phase was added into the oil phase, wherein a volume ratio of the aqueous phase to the oil phase was 1:1, and then emulsification was performed at 10000 r/min for 30 minutes to obtain a nanosphere emulsion.

In S3, a sodium hydroxide-n-propanol mixed solution was used as a precipitant, 10 mL of n-propanol was added with several drops of saturated sodium hydroxide solution to adjust a pH value to 8.5, then the mixed solution was evenly mixed and added into the nanosphere emulsion slowly, a volume ratio of the emulsifier to the precipitant was controlled to be 1.5:50, then a mixture obtained was stood for 2 minutes, and added with a proper amount of n-propanol for dehydration; and then the mixture was centrifuged at 2000 r/min for 5 minutes, cleaned, and dried, thus obtaining the chloroquine chitosan nanosphere, with a particle diameter ranging from 200 nm to 800 nm, and a loading rate of chloroquine of 10.3%.

Embodiment 3 Preparation of Chloroquine-Chitosan Nanosphere

1. Preparation Method

In S1, water-soluble chitosan was dissolved in water, then added with chloroquine sulfate, and evenly mixed and stirred to form an aqueous phase, and a mass ratio of the chloroquine sulfate to the water-soluble chitosan was controlled to be 1:7, wherein a degree of deacetylation of the water-soluble chitosan was 90%, and a viscosity-average molecular weight thereof was 4000.

In S2, olive oil was used as an oil phase matrix, and an emulsifier Tween-80 was added into the oil phase matrix to form an oil phase; and the aqueous phase was added into the oil phase, wherein a volume ratio of the aqueous phase to the oil phase was 1:6, and then emulsification was performed at 20000 r/min for 10 minutes to obtain a nanosphere emulsion.

In S3, a sodium hydroxide-n-propanol mixed solution was used as a precipitant, n-propanol was firstly added with several drops of saturated sodium hydroxide solution to adjust a pH value to 10, then the mixed solution was evenly mixed and added into the nanosphere emulsion slowly, a volume ratio of the emulsifier to the precipitant was controlled to be 1.5:30, then a mixture obtained was stood for 8 minutes, and added with a proper amount of n-propanol for dehydration; and then the mixture was centrifuged at 1500 r/min for 10 minutes, cleaned, and dried, thus obtaining the chloroquine chitosan nanosphere, with an average particle diameter of 400 nm, and a loading rate of chloroquine of 8.6%.

Embodiment 4 Preparation of Chloroquine-Chitosan Nanosphere Gel

1. Prescription of gel:

| | |
|---|---|
| Chloroquine-chitosan nanosphere | 1% |
| Carboxymethyl cellulose | 2% |
| Ethylparaben | 0.2% |

-continued

| | |
|---|---|
| Glycerol | 30% |
| Peppermint oil | 0.1% |
| Purified water | Supplemented to 100% |

2. The preparation method included the following steps.

(1) Preparation of nanosphere: the nanosphere was prepared according to the preparation steps of the chloroquine-chitosan nanosphere in the Embodiment 1.

(2) 20 g of carboxymethyl cellulose was added with 300 g of glycerol (prescription dosage) and 2 g of ethylparaben, then a mixture obtained was evenly stirred, and fully swelled, and used as a gel matrix; 10 g of the chloroquine-chitosan nanospheres were dissolved with 100 mL of water, added into the gel matrix in batches and stirred. 1 ml of peppermint oil was added, and water was added to 1000 mL to prepare an antibacterial and antiviral chloroquine-chitosan nanosphere gel suitable for external genitalia.

Figure 4:
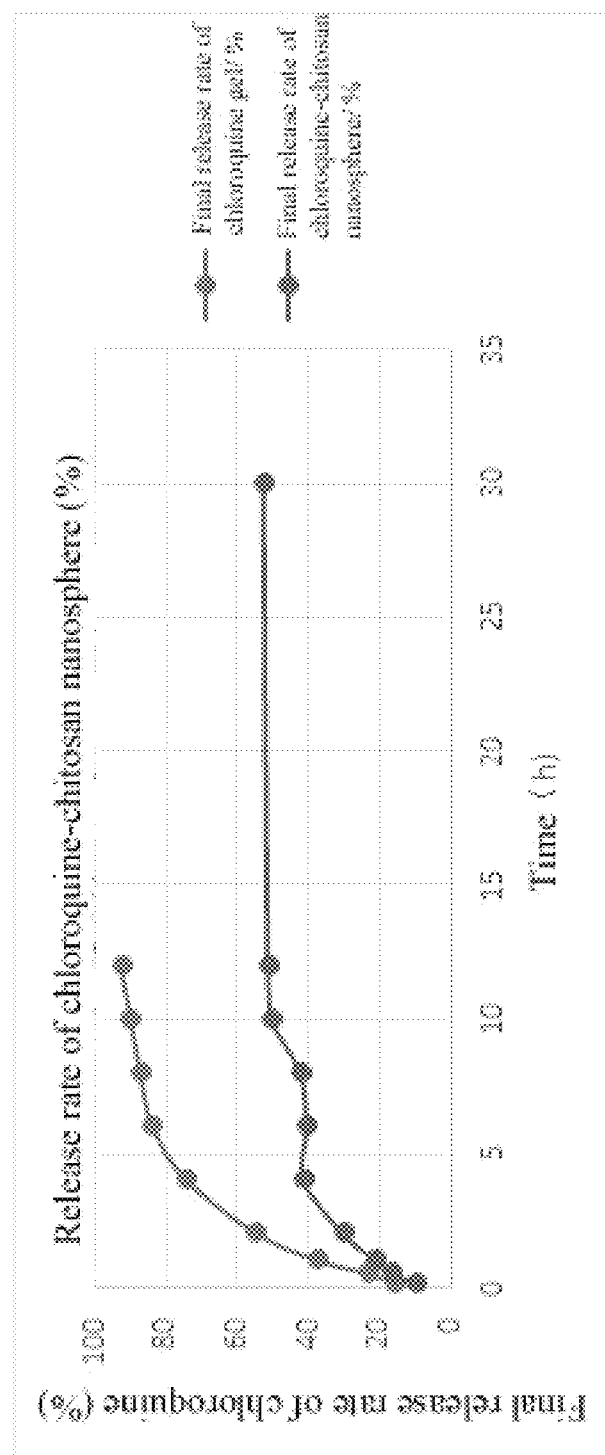
FIG. 4 shows drug release of the chloroquine-chitosan nanosphere and the chloroquine microsphere.

3. Pure chloroquine gel was prepared by the same method, and release rates of chloroquine in the chloroquine-chitosan nanosphere gel and the chloroquine gel were compared. As shown in FIG. 4, the chloroquine-chitosan nanosphere gel could slowly and stably release the chloroquine. The chloroquine-chitosan nanosphere gel prepared by the present invention has no sudden release phenomenon at the early stage, and a release speed of the chloroquine-chitosan nanosphere gel is almost not affected by a medium. The chloroquine-chitosan nanosphere gel presents a good slow release effect, which is beneficial for sustained release of a medicine after external administration.

Embodiment 5 Preparation of Chloroquine-Chitosan Nanosphere Gel

1. Prescription of gel:

| | |
|---|---|
| Chloroquine-chitosan nanosphere | 5% |
| Carboxymethyl cellulose | 0.5% |
| Ethylparaben | 0.5% |
| Glycerol | 30% |
| Peppermint oil | 0.1% |
| Purified water | Supplemented to 100% |

2. The preparation method included the following steps.

(1) Preparation of nanosphere: the nanosphere was prepared according to the preparation steps of the chloroquine-chitosan nanosphere in the Embodiment 1.

(2) Carboxymethyl cellulose was added with glycerol (prescription dosage) and 800 mL of water, then a mixture obtained was evenly stirred, and fully swelled, and used as a gel matrix; the chloroquine-chitosan nanospheres were dissolved with 100 mL of water, added into the gel matrix in batches and stirred. Ethylparaben was dissolved with 50 mL of hot water at 80° C. to 85° C., and added into the gel matrix when a temperature was reduced below 40° C., and stirred evenly. Peppermint oil was added, and water was added to 1000 mL to prepare an antibacterial and antiviral chloroquine-chitosan nanosphere gel suitable for external genitalia.

3. According to the steps above, with remaining process conditions unchanged, mass ratios of chloroquine phosphate to chitosan were changed to prepare gels 1, 2, 3 and 4 respectively; and meanwhile, according to the preparation steps of the embodiment above, with remaining process conditions unchanged, pure chitosan was used as a main active component to prepare gel 5, without adding with chloroquine or a chloroquine derivative, as shown in the following table.

TABLE 1

Results of Preparation of Nanosphere Gel with Different Ratios of Chloroquine to Chitosan

| | Mass ratio of chloroquine phosphate to chitosan | Character | pH value | Viscosity (mp/s) | Effective chloroquine content (%) |
|---|---|---|---|---|---|
| Gel 1 | 1:5 | Pale yellow semitransparent gel with even texture and faint mint fragrance, which can flow downwardly in a column | 4.27 | 11868 | 0.84 |
| Gel 2 | 1:3 | Beige non-transparent gel with even texture and faint mint fragrance, which can flow downwardly in a column | 4.08 | 9246 | 1.67 |
| Gel 3 | 1:1 | Beige non-transparent paste with faint mint fragrance and small particles | 3.97 | 6217 | 2.50 |
| Gel 4 | 1:0.5 | Earthy yellow non-transparent paste with faint mint fragrance and large particles | 3.77 | 5890 | 5.03 |
| Gel 5 | Pure chitosan | Orange transparent gel with faint mint fragrance and even texture | 4.79 | 20969 | 0 |

Figure 5:
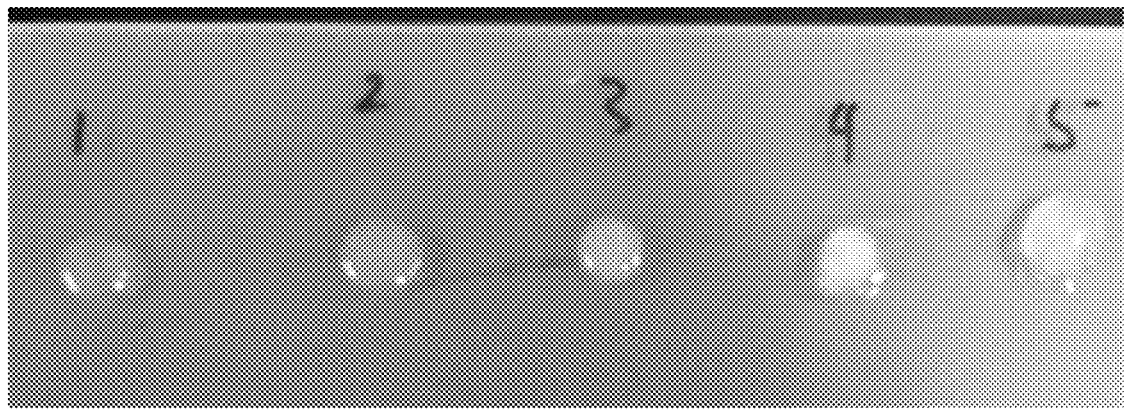
FIG. 5 shows gel products with different ratios observed on a smooth glass plane (a mass ratio of chloroquine phosphate to chitosan is respectively 1:5, 1:3, 1:1, 1:0.5 from No. 1 to No. 4 gel products, wherein No. 5 is a gel product of pure chitosan).
Figure 6:
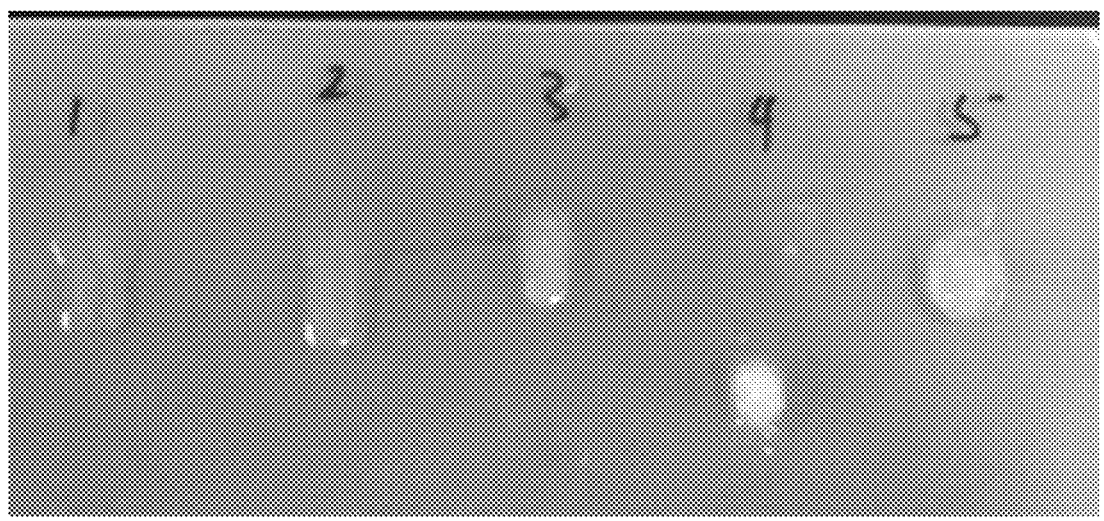
FIG. 6 shows flowing of the gel products with different ratios on the smooth glass plane in 1 minute (the mass ratio of the chloroquine phosphate to the chitosan is respectively 1:5, 1:3, 1:1, 1:0.5 from No. 1 to No. 4 gel products, wherein No. 5 is the gel product of pure chitosan).

FIG. 5 is a shape diagram of gel products with different ratios observed on a smooth glass plane (a mass ratio of chloroquine phosphate to chitosan is respectively 1:5, 1:3, 1:1, 1:0.5 from No. 1 to No. 4 gel products, wherein No. 5 is a product of pure chitosan); and FIG. 6 shows flowing of the gel products with different ratios on the smooth glass plane in 1 minute.

The experiment showed that when the ratio of the chloroquine phosphate to the chitosan was 1:1 or 1:0.5, the gel prepared was uneven in texture, had small particles, and had a poor fluidity. When the ratio of the chloroquine phosphate to the chitosan was 1:5 or 1:3, the product with gel of even texture, a pH suitable for vaginal and skin administration, a moderate viscosity, color and odor meeting the needs of different populations, and a stable chloroquine content was prepared. However, when the mass ratio of the chloroquine phosphate to the chitosan was 1:5, the chloroquine content was lower and a medicine effect was limited to a certain extent, and under comprehensive consideration, when the mass ratio of the chloroquine phosphate to the chitosan was 1:3, the product was better in performance.

Embodiment 6 Irritation Test of Chloroquine-Chitosan Nanosphere Gel on Damaged Skin 1. Experimental Method (1) New Zealand rabbits were used as experimental objects, left and right skins of the same body were compared with each other, a "Tic-Tac-Toe" symbol (with an area of about 3.0 cm×3.0 cm) was marked on skins of administration parts on left and right sides respectively by using an intra-individual left/right skin self-comparison method. 1.0 g of tested substance was given to the left side, wherein an administration dose was 9 cm$^2$/per rabbit, an application area of each time was 3.0 cm×3.0 cm. 1.0 g of white vaseline was given to the right side as a negative control side. Animals in each group were administered once a day for 28 consecutive days.

Groups of the tested substances were respectively as follows:

Group A: a control group, with a blank gel matrix,

Group B: a chloroquine-chitosan nanosphere gel group 1, wherein a mass ratio of chloroquine phosphate to chitosan was 1:3, Group C: a chloroquine-chitosan nanosphere gel group 2, wherein a mass ratio of chloroquine phosphate to chitosan was 1:5, Group D: a chloroquine-chitosan nanosphere gel group 3, wherein a mass ratio of chloroquine phosphate to chitosan was 1:0.5, and Group E: a chloroquine phosphate gel group.

Before each application, and 1 hour after each medicine removal, and 1 hour, 24 hours, 48 hours, 72 hours and 14 days after the last medicine removal on the 28$^{th}$ day, erythema and edema at the administration parts were observed and recorded respectively on each observation time point for the animals in each group above, and the erythema and the edema were scored. Meanwhile, it was necessary to observe whether pigmentation, bleeding point, skin roughness or skin thinning occurred at the administration parts, and to record occurrence and regression time of the pigmentation, the bleeding point, the skin roughness or the skin thinning.

(2) For the animals in the five groups above, left and right skins of the administration parts of the animals in each group were respectively subjected to histopathological examination on the 14$^{th}$ day after the last medicine removal.

2. Results (1) Skin Observation Results of Each Group

Test Results:

On the negative control side (right side), the skins of the administration parts of the animals in each tested substance group had no obvious irritation reaction on each observation time point, so that it could be judged that a result of a negative control substance (white vaseline) was negative.

Group A: no obvious irritant reaction was found on all the observation time points, so that it could be judged that the blank gel matrix had no irritation on skin.

Group B: the skins of the administration parts on the tested substance side (left side) of 6/6 animals had slight erythema or edema on the visual observation time point from the 1$^{st}$ day to the 12$^{th}$ day, no obvious abnormality was found in observation on the administration parts of each animal from the 12$^{th}$ day to the time before necropsy, and histopathological examination results of 72 hours after and the 14$^{th}$ day after the last medicine removal showed that the skins of the administration parts on the tested substance side of 6/6 animals had slight edema in 2 cases and no obvious abnormal change in other cases. Therefore, the irritation above tended to be judged in that the medicine slightly aggravated a mechanical stimulation after the skin was damaged.

Group C: the skins of the administration parts on the tested substance side (left side) of 6/6 animals had slight erythema or edema on a visual observation time point from the 1$^{st}$ day to the 12$^{th}$ day, no obvious abnormality was found in observation on the administration parts of each animal from the 12$^{th}$ day to the time before necropsy, and histopathological examination results of 72 hours after and the 14$^{th}$ day after the last medicine removal showed that the skins of the administration parts on the tested substance side of 6/6 animals had no obvious abnormal change. Therefore, the irritation above tended to be judged as a mechanical stimulation after the skin was damaged.

Group D: 4/6 of the administration parts on the tested substance side (left side) of the 6/6 animals had relatively obvious erythema or edema on the 12$^{th}$ day, scabs fell off during administration, the skin surfaces failed to completely heal when the scabs fell off, and wounds healed obviously 72 hours after the last medicine removal.

Group E: 4/6 of the damaged parts of the administration parts on the tested substance side (left side) of the 6/6 animals cracked on the 11$^{th}$ day, and tended to be outwards extended, the erythema or the edema at the administration parts was more obvious than that in the previous period, scabs were continuously regenerated and then fell off, and the skin surface failed to completely heal when the scabs fell off, which was significantly different from the negative control side (the intra-individual right side). Combined with the histopathological examination results of 72 hours after and the 14$^{th}$ day after the last medicine removal, the 6/6 animals had obvious abnormalities in the skins of the administration parts on the tested substance side, wherein 3 cases autopsied 72 hours after the last medicine removal showed a certain degree of damage, obvious thickening of an epidermal layer, disorder of arrangement of subepidermal connective tissues, proliferation of fibrous tissues, infiltration of inflammatory cells, scab of epidermis, depression of a part of epidermis, fuzzy structure, etc., and 3 cases autopsied on the 14$^{th}$ day after the last medicine removal showed local epidermal thickening, disorder of arrangement of subepidermal connective tissues, proliferation of fibrous tissues and infiltration of inflammatory cells.

It could be seen from the experimental results above that irritation of chloroquine phosphate chitosan nanosphere gel on the damaged skins was significantly lower than that of chloroquine phosphate gel (general external preparation) after multiple administration to the damaged skins of the New Zealand rabbits. For the chloroquine phosphate chitosan nanosphere gel, the lower the ratio of the chloroquine/nanosphere carrier was, the smaller the irritation reaction on the skin was, and the better the repair of the damaged skin after stopping administration was. However, the chloroquine gel could cause worse damage on the damaged skins, when the negative control side was completely repaired, the skins on the chloroquine gel side could not be repaired normally, and the skins on the chloroquine gel side could only recover to a certain extent 14 days after stopping administration, with an obvious difference, which indicated that the chloroquine had an irritation effect on the damaged skins, and the chloroquine-chitosan nanosphere could significantly reduce the irritation effect, which might be related to antibacterial, anti-inflammatory and wound healing promoting effects of the chitosan itself.

(2) Pathological Examination Results

Figure 7:
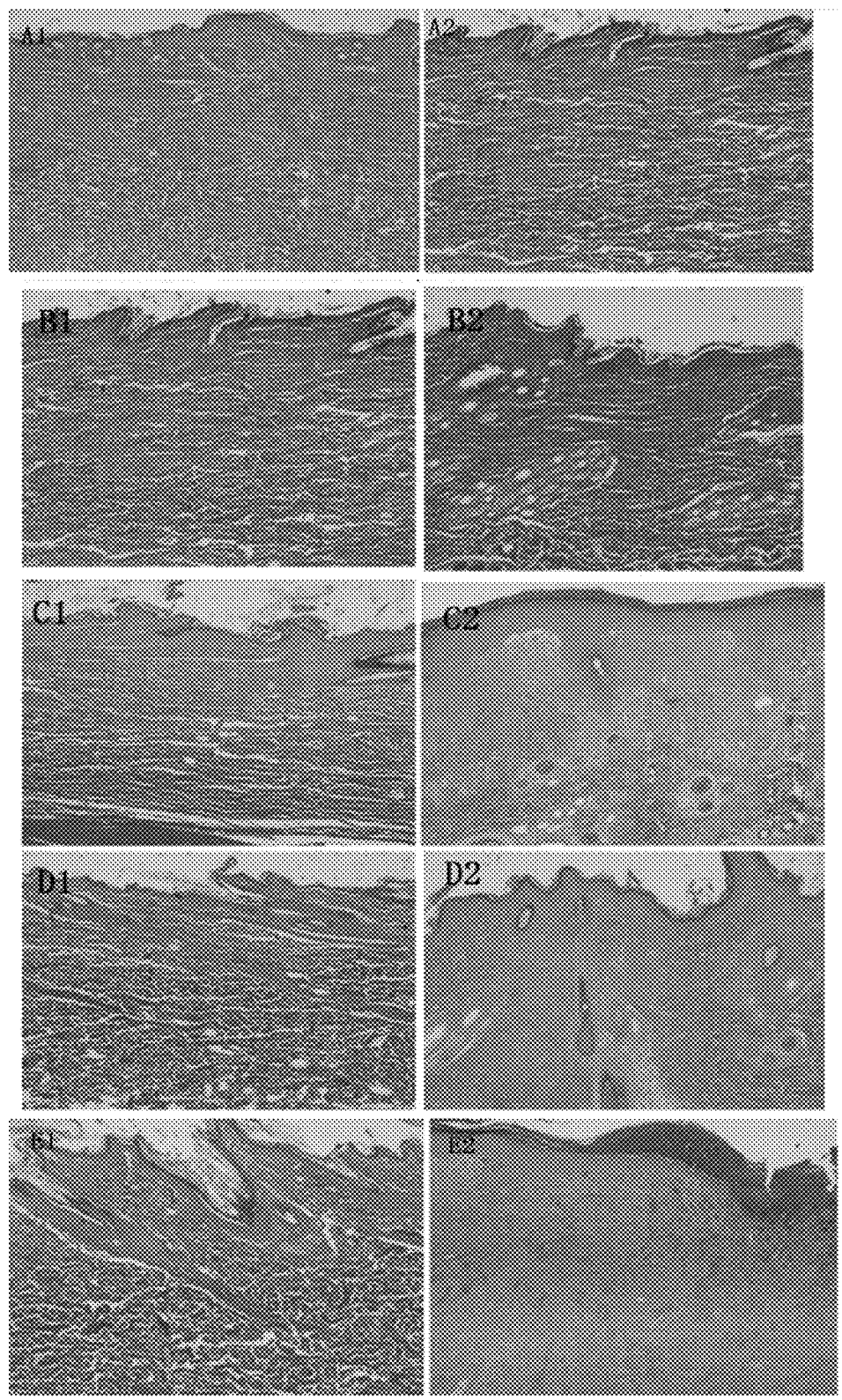
FIG. 7 shows H-E staining results of an irritation test on damaged skin, wherein Group A is a control group with a blank gel matrix, including A1 of FIG. 7 (tested substance side) and A2 of FIG. 7 (negative control side); Group B is a chloroquine-chitosan nanosphere gel group 1 with a mass ratio of chloroquine phosphate to chitosan being 1:3, including B1 of FIG. 7 (tested substance side) and B2 of FIG. 7 (negative control side); Group C is a chloroquine-chitosan nanosphere gel group 2 with a mass ratio of chloroquine phosphate to chitosan being 1:5, including C1 of FIG. 7 (tested substance side) and C2 of FIG. 7 (negative control side); Group D is a chloroquine-chitosan nanosphere gel group 3 with a mass ratio of chloroquine phosphate to chitosan being 1:0.5, including D1 of FIG. 7 (tested substance side) and D2 of FIG. 7 (negative control side); and Group E is a chloroquine phosphate gel group, including E1 of FIG. 7 (tested substance side) and E2 of FIG. 7 (negative control side).

Group A: as shown in A1 (blank matrix side) and A2 (negative control side) in FIG. 7, skin epidermis, dermis and accessories were in good condition structurally, and inflammatory cell infiltration and small vessel dilatation were not found.

Group B: as shown in B1 (chloroquine-chitosan nanosphere gel) and B2 (negative control side) in FIG. 7, B2 of FIG. 7 showed that the skin epidermis, the dermis and the accessories were in good condition structurally, and the inflammatory cell infiltration and the small vessel dilatation were not found. Compared with the negative control side, B1 of FIG. 7 showed that a small focal epidermal layer of the skins in the group was slightly thickened, with infiltration of a small number of inflammatory cells.

Group C: as shown in C1 (chloroquine-chitosan nanosphere gel side) and C2 (negative control side) in FIG. 7, C2 of FIG. 7 showed that the skin epidermis, the dermis and the accessories were in good condition structurally, and the inflammatory cell infiltration and the small vessel dilatation were not found. C1 of FIG. 7 showed that a local epidermal layer of the skins in the group was slightly thickened, a number of cell layers was obviously increased, and the cells grew extendedly to a dermis layer; and arrangement of subepidermal connective tissues was disordered, with infiltration of some inflammatory cells.

Group D: as shown in D1 (chloroquine-chitosan nanosphere gel side) and D2 (negative control side) in FIG. 7, D2 of FIG. 7 showed that the skin epidermis, the dermis and the accessories were in good condition structurally, and the inflammatory cell infiltration and the small vessel dilatation were not found. Compared with the negative control side, D1 of FIG. 7 showed that the local epidermal layer in the group was slightly thickened, and the number of the cell layers was increased, with infiltration of a small number of inflammatory cells.

Group E: as shown in E1 (chloroquine gel side) and E2 (negative control side) in FIG. 7, on the negative control side, the skin epidermis, the dermis and the accessories were in good condition structurally, the inflammatory cell infiltration and the small vessel dilatation were not found, while a local epidermal layer of the skins on the chloroquine gel side had scabs, and the epidermis was obviously thickened; a part of scab skins were closely connected with a subcutaneous tissue, the epidermal layer was sunken, a structure was fuzzy, and a large number of inflammatory cells were infiltrated with fibrous tissue hyperplasia; a number of hair follicles in a dermal layer was decreased significantly; and however, no obvious abnormality was found in a muscular layer and the subcutaneous tissue.

The pathological examination results above showed that compared with the chloroquine gel, gel of the chloroquine-chitosan nanosphere group had obvious advantages in irritation and healing after medicine withdrawal. In each chloroquine-chitosan nanosphere group, the lower the ratio of the chloroquine to the nanosphere carrier was, the smaller the irritation reaction to the skin was.

According to the skin observation results and the pathological examination results, the irritation reaction of the chloroquine-chitosan nanosphere gel on the skins was obviously smaller than that of the chloroquine gel, which indicated that the chloroquine-chitosan nanosphere greatly reduced an irritation side effect of the chloroquine on the skins and promoted wound healing to a certain extent. When a mass ratio of the chloroquine to the chitosan was not more than 1:3, an irritation effect was smaller and a medicine content was the highest.

Embodiment 7 Animal Test on Herpes Virus Vaginitis

1. Experimental Method

The chloroquine-chitosan nanosphere obtained in the Embodiment 1 was made into gel for the animal test on herpes virus vaginitis.

The specific experimental method was that: a number of Hartley guinea pigs qualified for adaptive observation were selected, 10 animals were randomly selected as a blank control group (A), and the other animals were all infected with herpes virus through vagina for modeling. After modeling, the animals were randomly divided into five groups, and the overall grouping was as follows:

Group A: a blank control group,

Group B: a model group,

Group C: a chloroquine-chitosan nanosphere gel group 1, wherein a mass ratio of chloroquine phosphate to chitosan was 1:3, Group D: a chloroquine-chitosan nanosphere gel group 2, wherein a mass ratio of chloroquine phosphate to chitosan was 1:0.5, and Group E: a chloroquine phosphate gel group.

10 animals in each group were administrated vaginally. The blank control group and the model control group were given 0.9% sodium chloride injection, while the Groups C, D and E were given corresponding tested medicine once a day for two weeks. 14 days after administration, a vaginal mucosa tissue was taken for fixing and embedding the next day, paraffin wax was continuously cut into sections of 4 μm, and after hematoxylin-eosin (HE) staining, a pathological condition of the vaginal mucosa tissue was observed under a microscope.

2. Results (1) Pathological Examination

Figure 8:
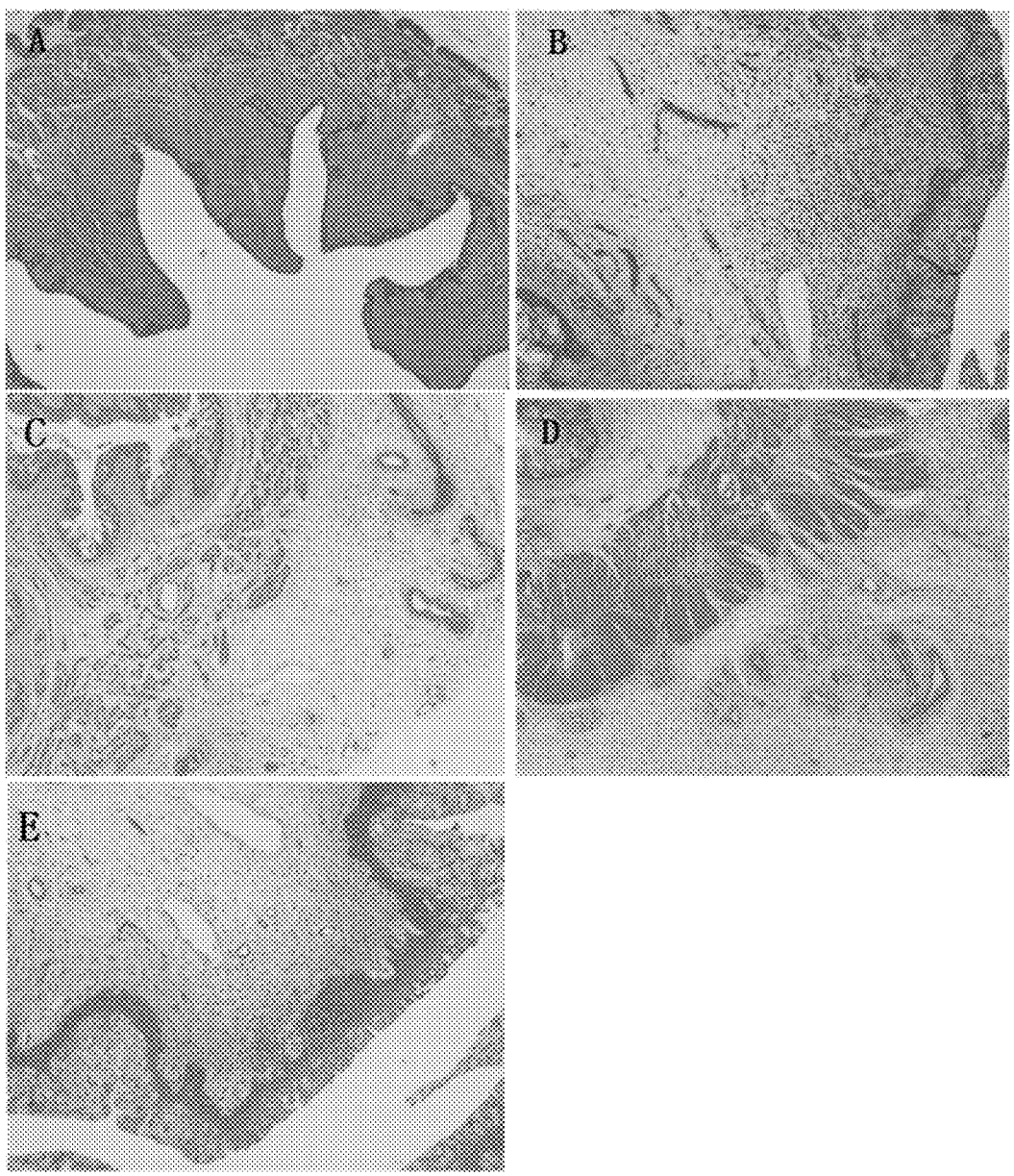
FIG. 8 shows H-E staining results of an animal test on herpes virus vaginitis, wherein A of FIG. 8 is a blank control group; B of FIG. 8 is a model control group; C of FIG. 8 is a chloroquine-chitosan nanosphere gel group 1 with a mass ratio of chloroquine phosphate to chitosan being 1:3; and D of FIG. 8 is a chloroquine-chitosan nanosphere gel group 2 with a mass ratio of chloroquine phosphate to chitosan being 1:0.5; and E of FIG. 8 is a chloroquine phosphate gel group.

Group A: results of the blank control group are shown in A in FIG. 8, wherein a vaginal mucosa epithelial cell of the blank control group had a complete structure, and a lamina propria vessel had no dilatation and inflammatory cell infiltration.

Group B: results of the model control group are shown in B in FIG. 8, wherein a submucosal lamina propria of vagina in the model control group had infiltration of a large number of inflammatory cells, disordered arrangement of loose connective tissues and obvious edema.

Group C: results of the chloroquine-chitosan nanosphere gel group 1, wherein the mass ratio of the chloroquine phosphate to the chitosan was 1:3, is shown in C in FIG. 8, wherein connective tissues of a serosal layer of the group were increased, and disordered in arrangement, with obvious edema and infiltration of a small number of inflammatory cells.

Group D: results of the chloroquine-chitosan nanosphere gel group 2, wherein the mass ratio of the chloroquine phosphate to the chitosan was 1:0.5, is shown in D in FIG. 8, wherein a submucosal lamina propria of the group had obvious edema, and connective tissues of the serosal layer were increased, and disordered in arrangement, with obvious edema and inflammatory cell infiltration.

Group E: results of the chloroquine phosphate gel group are shown in E in FIG. 8, wherein local epithelial cells of vaginal mucosa of the chloroquine gel group were deformed and necrotic, and loose connective tissues in the submucosal lamina propria were slightly disordered, with obvious edema and inflammatory cell infiltration.

(2) Lesion Degree Results of Tested Animals in Histological Examination

TABLE 3

Lesion Degree Statistical Table of Tested Animals in Histological Examination

|  |  | Vagina | | |
| --- | --- | --- | --- | --- |
| Group | Lesion degree | Disordered loose connective tissues of lamina propria and edema | Thickened serosal layer and edema | Inflammatory cell infiltration of lamina propria |
| Blank | − | 10/10 | 10/10 | 10/10 |
| control | ± | 0/10 | 0/10 | 0/10 |
| group A | + | 0/10 | 0/10 | 0/10 |
|  | ++ | 0/10 | 0/10 | 0/10 |
|  | +++ | 0/10 | 0/10 | 0/10 |
| Model | − | 0/10 | 2/10 | 2/10 |
| control | ± | 2/10 | 3/10 | 4/10 |
| group B | + | 5/10 | 3/10 | 2/10 |
|  | ++ | 3/10 | 2/10 | 2/10 |
|  | +++ | 0/10 | 0/10 | 0/10 |
| Chloroquine- | − | 4/10 | 9/10 | 4/10 |
| chitosan | ± | 3/10 | 0/10 | 3/10 |
| nanosphere | + | 2/10 | 0/10 | 3/10 |
| gel group C | ++ | 1/10 | 1/10 | 0/10 |
|  | +++ | 0/10 | 0/10 | 0/10 |
| Chloroquine- | − | 2/10 | 8/10 | 5/10 |
| chitosan | ± | 2/10 | 0/10 | 4/10 |
| nanosphere | + | 3/10 | 1/10 | 1/10 |
| gel group D | ++ | 3/10 | 0/10 | 0/10 |
|  | +++ | 0/10 | 1/10 | 0/10 |
| Chloroquine | − | 1/10 | 6/10 | 4/10 |
| phosphate | ± | 3/10 | 0/10 | 4/10 |
| group E | + | 1/10 | 3/10 | 2/10 |
|  | ++ | 4/10 | 0/10 | 0/10 |
|  | +++ | 1/10 | 1/10 | 0/10 |

Note:
"−" indicates that a tissue structure has no obvious abnormality; "±" indicates extremely mild injury; "+" indicates mild injury; "++" indicates moderate injury; and "++" indicates serious injury.

The research results above showed that compared with the chloroquine gel, the chloroquine-chitosan nanosphere gel could obviously improve vaginitis caused by herpes virus. A degree of inflammation of each group was compared: the model control group>the chloroquine phosphate group E>the chloroquine-chitosan nanosphere gel group D>the chloroquine-chitosan nanosphere gel group C>the blank control group. Moreover, the combined application of chloroquine and chitosan could significantly improve vaginal edema, and the results were similar to the degree of inflammation, which indicated that the combined application of the chloroquine and the chitosan had a significant increased therapeutic effect.

Embodiment 8 Treatment of Condyloma Acuminatum Caused by HPV

1. Experimental Method

A plurality of nude mice (half male and half female) qualified for adaptive observation were selected, HPV-infected wart tissues were directly inoculated to the nude mice subcutaneously. A transplantation process was strictly in accordance with a principle of aseptic operation. 5 days to 6 days after inoculation of warts, the nude mice with good inoculated parts were selected and randomly and evenly divided into 4 groups according to body weight and gender, namely:

Group A: a model control group,

Group B: a chloroquine-chitosan nanosphere gel group 1, wherein a mass ratio of chloroquine phosphate to chitosan was 1:3, Group C: a chloroquine-chitosan nanosphere gel group 2, wherein a mass ratio of chloroquine phosphate to chitosan was 1:0.5, and Group D: a chloroquine phosphate gel group.

Each group had 6 nude mice (half male and half female). The model control group was given white vaseline and other groups were all given corresponding gels. Each group was administrated through skin, and a corresponding administration area on administration parts of animals was about 2 cm×2 cm. The medicine was administrated once a day, with 6 hours for each contact, and after 6 hours of contact, the medicine was removed. The administration was continuously performed for 14 days. 14 days after administration, a wart tissue was taken for fixing and embedding the next day, paraffin wax was continuously cut into sections of 4 μm, and after hematoxylin-eosin (HE) staining, a pathological condition of the wart tissue was observed under a microscope.

2. Results

Pathological Examination Results:

(1) Results of warts of Group A showed that the wart tissue could be seen in each animal, an epithelial cell structure of the wart tissue was complete, and a koilocytoid cell could be seen locally.

Figure 9:
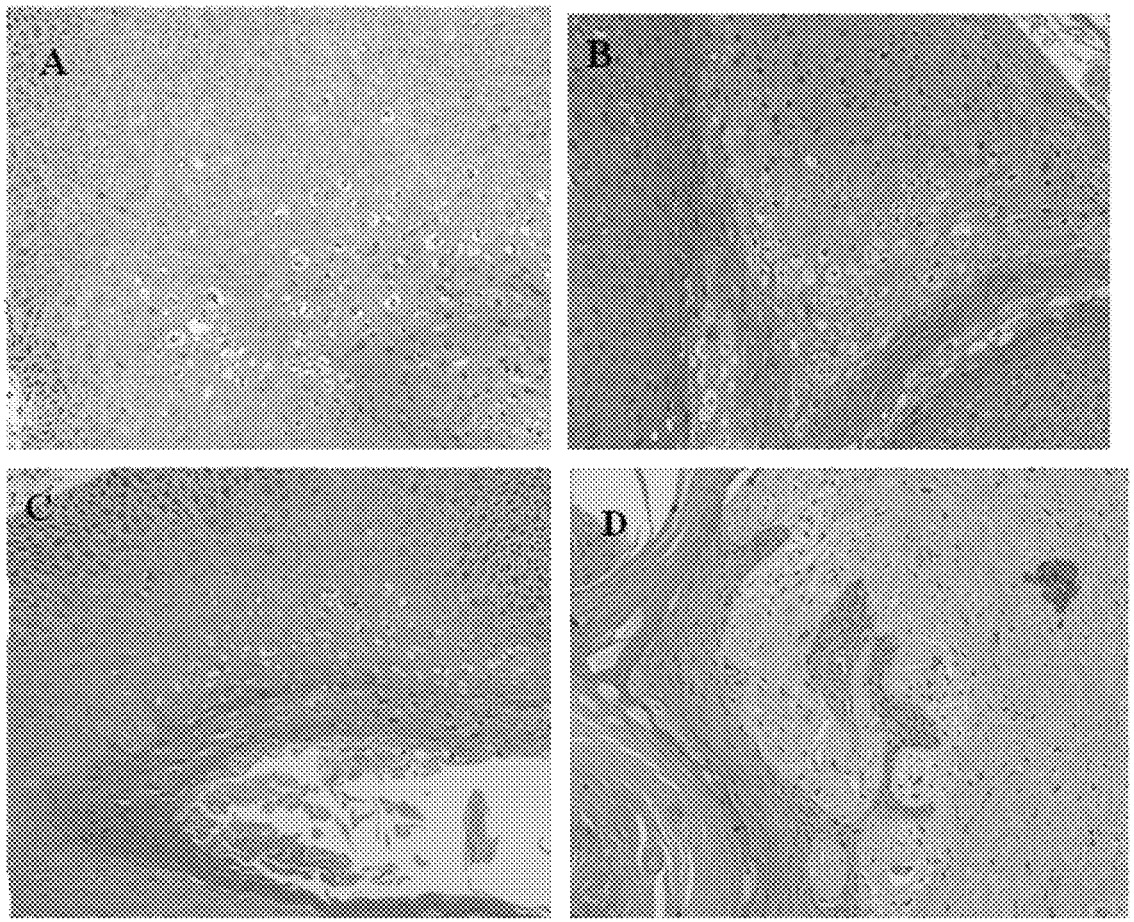
FIG. 9 shows H-E staining results of an animal test on HPV condyloma acuminatum, wherein A of FIG. 9 is a model control group; B of FIG. 9 is a chloroquine-chitosan nanosphere gel group 1 with a mass ratio of chloroquine phosphate to chitosan being 1:3; C of FIG. 9 is a chloroquine chitosan nanosphere gel group 2 with a mass ratio of chloroquine phosphate to chitosan being 1:0.5; and D of FIG. 9 is a chloroquine phosphate gel group.

As shown in A in FIG. 9, for the warts, obvious vacuoles existed around a nucleus of a local epithelial cell, with an obvious nucleolus. (H-E staining ×200)

(2) Results of warts of Group B showed that the wart tissue could be seen in 6 animals. Epithelial cells of wart tissues of 2 animals (03 and 04; 2/6) were degenerated and necrotic locally, and a few koilocytoid cells could be seen; and epithelial cells of wart tissues of 4 animals (01, 02, 05 and 06; 4/6) were complete in structure, and koilocytoid cells could be seen locally.

As shown in B in FIG. 9, for the warts, obvious vacuoles existed around a nucleus of a local epithelial cell, with an obvious nucleolus. (H-E staining ×200)

(3) Results of warts of Group C showed that the wart tissue could be seen in 6 animals. Epithelial cells of wart tissues of 3 animals (03, 04 and 05; 3/6) were degenerated and necrotic locally, and a few koilocytoid cells could be seen; and epithelial cells of wart tissues of 3 animals (01, 02 and 06; 3/6) were complete in structure, and koilocytoid cells could be seen locally.

As shown in C in FIG. 9, for the warts, obvious vacuoles existed around a nucleus of a local epithelial cell, with an obvious nucleolus. (H-E staining ×200)

(4) Results of warts of Group D showed that the wart tissue could be seen in 6 animals. Epithelial cells of wart tissues of 4 animals (01, 02, 03 and 04; 4/6) were degenerated and necrotic locally, and a few koilocytoid cells could be seen; and epithelial cells of wart tissues of 2 animals (05 and 06; 2/6) were complete in structure, and koilocytoid cells could be seen locally.

As shown in D in FIG. 9, for the warts, the epidermal cells of the warts had hyperkeratosis, squamous epithelium could be seen under epidermis, the epithelial cells were degenerated and necrotic locally, and a few koilocytoid cells could be seen locally.

The research results above showed that chloroquine had an effect of clearing viruses of infected cell for the warts caused by HPV, and with the increase of a chloroquine content, a number of koilocytoid cells infected with HPV was decreased. The chloroquine gel group (Group D) could obviously remove infected cells, but could cause local degeneration and necrosis of tissues. Compared with pure chloroquine gel, the chloroquine-chitosan gel could protect skin while reducing the infected cells.

Embodiment 9 Killing or Inhibiting Effect on Various Vaginal Pathogenic Microorganisms In-vitro antibacterial activity detection was performed on the chloroquine-chitosan nanosphere gel group (Group B: chloroquine-chitosan nanosphere gel, wherein a mass ratio of chloroquine phosphate to chitosan was 3:1) in the Embodiment 6. 20 g of gel product was added into 100 mL of pH 7.0 buffer (negative control was not added with a test sample) to fully dissolve the gel product. 1 mL, 0.5 mL, 0.25 mL and 0.125 mL of pH 7.0 buffers added with the test sample were added into corresponding culture mediums of corresponding bacteria, and cultured in a plate. *Pseudomonas aeruginosa, Candida albicans, Escherichia coli* and *Staphylococcus aureus* were resuscitated and diluted, and when a bacterial concentration was 100 cfu/mL, each culture medium was inoculated with an inoculating loop, and observation was started after culturing for 5 days to 7 days.

In-vitro antibacterial activity detection results showed that the chitosan-chloroquine nanosphere gel with different concentrations could inhibit growth of the *Pseudomonas aeruginosa*, the *Candida albicans*, the *Escherichia coli* and the *Staphylococcus aureus*, and the higher the concentration is, the higher the inhibition rate of bacteria is. Particularly, *Candida albicans* and *Staphylococcus aureus* are more sensitive.

The results showed that the chloroquine-chitosan nanosphere gel had a good inhibition effect on various bacteria, but different sensitivities.

According to the present invention, the chloroquine and the chitosan were jointly applied, which had a synergistic inhibition effect on various vaginal pathogenic microorganisms. The medicine of the present invention could kill or inhibit various vaginal pathogenic microorganisms, such as *Staphylococcus aureus* (SA), *Pseudomonas aeruginosa*, beta Hemolytic *streptococcus* (ST), *Candida albicans* (CA), *Ureaplasma urealyticum* (Uu), *Trichomonas vaginalis* and *Bacteroides fragilis*, and herpes simplex virus type 2 (HSV-2). In addition, the medicine of the present invention could inhibit adhesion of a pathogen and a vaginal epithelial cell of a host, and prevent and treat various vaginitis, such as *Candida albicans* vaginitis, trichomonal vaginitis, bacterial vaginosis, genital herpes virus and other external genitalia infections.

Embodiment 10 Preliminary Clinical Research Results

It was found from application of the chloroquine-chitosan nanosphere of the present invention to 10 women suffering from vaginitis caused by candida infection that no patient reported a side effect and an adverse reaction in a treatment process, and no side effect and adverse reaction were found after 6 months of follow-up, and a total effective rate of the chloroquine-chitosan nanosphere treatment group was obviously increased by 30% compared with that of the chloroquine treatment group alone.

The present invention was applied to treatment of warts of 30 patients caused by HPV infection, and after 2 weeks to 3 weeks of treatment, the warts of the 30 patients were found to naturally fall off without any adverse reactions.

The chloroquine nanosphere of the present invention has good therapeutic effects on external genitalia infection including viral vaginitis, condyloma acuminatum, bacterial vaginosis, fungal-infectious vaginitis or trichomonal vaginitis, and other cutaneous warts including flat warts and warts at non-genital parts caused by HPV infection.

Obviously, the above-mentioned embodiments of the invention are merely examples for clearly illustrating the invention, but are not intended to limit the implementations of the invention. For those of ordinary skills in the art, other different forms of changes or variations can be made on the basis of the above description. It is not necessary or possible to exhaust all the implementations here. Any change, equivalent substitution, and improvement made within the spirit and principle of the invention shall fall within the scope of protection of the claims of the invention.

What is claimed is:

1. A chloroquine nanosphere, wherein the chloroquine nanosphere comprises a water-soluble nanosphere carrier, and chloroquine or a chloroquine derivative; a mass ratio of the chloroquine or the chloroquine derivative to the water-soluble nanosphere carrier during preparation ranges from 1:3 to 1:5; a loading rate of the chloroquine or the chloroquine derivative in the prepared chloroquine nanosphere ranges from 3.0% to 21.6%;

the water-soluble nanosphere carrier is water-soluble chitosan; a deacetylation degree of the water-soluble chitosan ranges from 80% to 95%, and a viscosity-average molecular weight thereof ranges from 3000 to 5000 g/mol; and the chloroquine derivative is selected from one or more of hydroxychloroquine, chloroquine phosphate or chloroquine sulfate.

2. The chloroquine nanosphere according to claim 1, wherein a preparation method thereof comprises the following steps:

S1: after dissolving the water-soluble nanosphere carrier, adding the chloroquine or the chloroquine derivative, and evenly mixing and stirring to form an aqueous phase;

S2: adding an emulsifier into an oil phase matrix to form an oil phase; adding the aqueous phase into the oil phase, wherein a volume ratio of the aqueous phase to the oil phase is 1:1 to 1:6; and emulsifying at 10000-20000 r/min for 10-30 minutes to obtain a nanosphere emulsion; and S3: adding a precipitant into the nanosphere emulsion, after evenly mixing, standing for 2-8 minutes, then dehydrating, performing high-speed centrifugation and cleaning, and drying to obtain the chloroquine nanosphere; wherein conditions for the high-speed centrifugation is to centrifuge at 1500-2000 r/min for 5-10 minutes;

the oil phase matrix is selected from one or more of corn oil, olive oil, peanut oil, soybean oil, or rapeseed oil;

the emulsifier is selected from one or more of Tween-20, Tween-80 or Span 80;

the precipitant is a sodium hydroxide-n-propanol mixed solution.

3. The chloroquine nanosphere according to claim 2, wherein a volume ratio of the emulsifier to the precipitant is (1-1.5):(30-50).

4. The chloroquine nanosphere according to claim 2, wherein a pH value of the precipitant ranges from 8.5 to 10.0.

* * * * *